(12) United States Patent
Sowards et al.

(10) Patent No.: US 12,048,491 B2
(45) Date of Patent: Jul. 30, 2024

(54) ULTRASOUND PROBE WITH TARGET TRACKING CAPABILITY

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/538,911

(22) Filed: Nov. 30, 2021

(65) Prior Publication Data

US 2022/0168050 A1 Jun. 2, 2022

Related U.S. Application Data

(60) Provisional application No. 63/119,829, filed on Dec. 1, 2020.

(51) Int. Cl.
*A61B 8/00* (2006.01)
*A61B 8/08* (2006.01)
*A61B 34/20* (2016.01)

(52) U.S. Cl.
CPC ............ *A61B 34/20* (2016.02); *A61B 8/0841* (2013.01); *A61B 8/085* (2013.01); *A61B 8/4472* (2013.01);
(Continued)

(58) Field of Classification Search
CPC ....... A61B 34/20; A61B 8/0841; A61B 8/085; A61B 8/4472; A61B 8/463; A61B 8/5207; A61B 2034/2063
See application file for complete search history.

(56) References Cited

U.S. PATENT DOCUMENTS 3,697,917 A 10/1972 Orth et al.
5,148,809 A 9/1992 Biegeleisen-Knight et al.
(Continued)

FOREIGN PATENT DOCUMENTS

CN 102871645 A 1/2013
CN 105107067 B 5/2018
(Continued)

OTHER PUBLICATIONS

Lu Zhenyu et al "Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).
(Continued)

*Primary Examiner* — Jeffrey G Hoekstra
*Assistant Examiner* — Amal Aly Farag
(74) *Attorney, Agent, or Firm* — Rutan & Tucker LLP

(57) ABSTRACT

An ultrasound imaging system is disclosed that can include an ultrasound probe including a transducer array configured to acquire ultrasound images, and a console including a processor and non-transitory computer-readable medium having stored thereon a plurality of logic modules that, when executed by the processor, are configured to perform operations including receiving an ultrasound image, detecting one or more targets within the ultrasound image, and generating a visualization from the ultrasound image to center the one or more detected targets within a displayed portion of the ultrasound image. Generating the visualization may include cropping the ultrasound image to center the one or more detected targets within a displayed portion of the ultrasound image. Generating the visualization may include increasing a magnification of a cropped portion of the ultrasound image
(Continued)

to center the one or more detected targets within a displayed portion of the ultrasound image.

26 Claims, 7 Drawing Sheets

(52) U.S. Cl.
CPC ............ *A61B 8/463* (2013.01); *A61B 8/5207* (2013.01); *A61B 2034/2063* (2016.02)

(56) References Cited

U.S. PATENT DOCUMENTS

| | | | |
|---|---|---|---|
| 5,181,513 A | 1/1993 | Touboul et al. |
| 5,325,293 A | 6/1994 | Dorne |
| 5,349,865 A | 9/1994 | Kavli et al. |
| 5,441,052 A | 8/1995 | Miyajima |
| 5,549,554 A | 8/1996 | Miraki |
| 5,573,529 A | 11/1996 | Haak et al. |
| 5,775,322 A | 7/1998 | Silverstein et al. |
| 5,879,297 A | 3/1999 | Haynor et al. |
| 5,897,503 A | 4/1999 | Lyon et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,733,458 B1 | 5/2004 | Steins et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,038,619 B2 | 10/2011 | Steinbacher |
| 8,060,181 B2 | 11/2011 | Rodriguez Ponce et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,199,082 B1 | 12/2015 | Yared et al. |
| 9,204,858 B2 | 12/2015 | Pelissier et al. |
| 9,220,477 B2 | 12/2015 | Urabe et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,449,330 B2 | 10/2019 | Newman et al. |
| 10,524,691 B2 | 1/2020 | Newman et al. |
| 10,751,509 B2 | 8/2020 | Misener |
| 11,564,861 B1 | 1/2023 | Gaines |
| 2002/0038088 A1 | 3/2002 | Imran et al. |
| 2003/0047126 A1 | 3/2003 | Tomaschko |
| 2003/0106825 A1 | 6/2003 | Molina et al. |
| 2003/0120154 A1 | 6/2003 | Sauer et al. |
| 2003/0125629 A1 | 7/2003 | Ustuner |
| 2003/0135115 A1 | 7/2003 | Burdette et al. |
| 2003/0149366 A1 | 8/2003 | Stringer et al. |

(56) References Cited

U.S. PATENT DOCUMENTS

| | | |
|---|---|---|
| 2004/0015080 A1 | 1/2004 | Kelly et al. |
| 2004/0055925 A1 | 3/2004 | Franks-Farah et al. |
| 2004/0197267 A1 | 10/2004 | Black et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0004290 A1 | 1/2006 | Smith et al. |
| 2006/0013523 A1 | 1/2006 | Childlers et al. |
| 2006/0015039 A1 | 1/2006 | Cassidy et al. |
| 2006/0020204 A1* | 1/2006 | Serra ............... G01S 7/5208 600/437 |
| 2006/0047617 A1 | 3/2006 | Bacioiu et al. |
| 2006/0079781 A1 | 4/2006 | Germond-Rouet et al. |
| 2006/0111634 A1* | 5/2006 | Wu ................. A61B 8/467 600/443 |
| 2006/0184029 A1* | 8/2006 | Haim ............. A61B 8/0833 600/443 |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0167738 A1 | 7/2007 | Timinger et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2007/0287886 A1 | 12/2007 | Saadat |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0108930 A1 | 5/2008 | Weitzel et al. |
| 2008/0125651 A1 | 5/2008 | Watanabe et al. |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0012401 A1 | 1/2009 | Steinbacher |
| 2009/0074280 A1 | 3/2009 | Lu et al. |
| 2009/0124903 A1 | 5/2009 | Osaka |
| 2009/0137887 A1 | 5/2009 | Shariati et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0281413 A1 | 11/2009 | Boyden et al. |
| 2009/0306509 A1 | 12/2009 | Pedersen et al. |
| 2010/0010348 A1* | 1/2010 | Halmann ........... A61B 8/466 600/443 |
| 2010/0211026 A2 | 8/2010 | Sheetz et al. |
| 2010/0249598 A1 | 9/2010 | Smith et al. |
| 2010/0286515 A1 | 11/2010 | Gravenstein et al. |
| 2010/0312121 A1 | 12/2010 | Guan |
| 2010/0324423 A1 | 12/2010 | El-Aklouk et al. |
| 2011/0002518 A1 | 1/2011 | Ziv-Ari et al. |
| 2011/0026796 A1* | 2/2011 | Hyun ............... A61B 8/5223 600/443 |
| 2011/0071404 A1 | 3/2011 | Schmitt et al. |
| 2011/0074244 A1 | 3/2011 | Osawa |
| 2011/0087107 A1 | 4/2011 | Lindekugel et al. |
| 2011/0166451 A1 | 7/2011 | Blaivas et al. |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0165679 A1 | 6/2012 | Orome et al. |
| 2012/0179038 A1 | 7/2012 | Meurer et al. |
| 2012/0179042 A1 | 7/2012 | Fukumoto et al. |
| 2012/0179044 A1 | 7/2012 | Chiang et al. |
| 2012/0197132 A1 | 8/2012 | O'Connor |
| 2012/0220865 A1 | 8/2012 | Brown et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0197367 A1 | 8/2013 | Smok et al. |
| 2013/0218024 A1 | 8/2013 | Boctor et al. |
| 2013/0323700 A1 | 12/2013 | Samosky et al. |
| 2013/0338503 A1 | 12/2013 | Cohen et al. |
| 2013/0338508 A1 | 12/2013 | Nakamura et al. |
| 2014/0005530 A1 | 1/2014 | Liu et al. |
| 2014/0031694 A1 | 1/2014 | Solek |
| 2014/0066779 A1 | 3/2014 | Nakanishi |
| 2014/0073976 A1 | 3/2014 | Fonte et al. |
| 2014/0100440 A1 | 4/2014 | Cheline et al. |
| 2014/0114194 A1 | 4/2014 | Kanayama et al. |
| 2014/0180098 A1 | 6/2014 | Flaherty et al. |
| 2014/0180116 A1 | 6/2014 | Lindekugel et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276069 A1 | 9/2014 | Amble et al. |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2014/0357994 A1 | 12/2014 | Jin et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1 | 7/2015 | Burkholz et al. |
| 2015/0209510 A1 | 7/2015 | Burkholz et al. |
| 2015/0209526 A1 | 7/2015 | Matsubara et al. |
| 2015/0282890 A1* | 10/2015 | Cohen ............. A61B 5/1128 600/424 |
| 2015/0297097 A1 | 10/2015 | Matsubara et al. |
| 2015/0359520 A1 | 12/2015 | Shan et al. |
| 2015/0359991 A1 | 12/2015 | Dunbar et al. |
| 2016/0000367 A1 | 1/2016 | Lyon |
| 2016/0026894 A1 | 1/2016 | Nagase |
| 2016/0029995 A1 | 2/2016 | Navratil et al. |
| 2016/0113699 A1 | 4/2016 | Sverdlik et al. |
| 2016/0120607 A1 | 5/2016 | Sorotzkin et al. |
| 2016/0157831 A1 | 6/2016 | Kang et al. |
| 2016/0166232 A1 | 6/2016 | Merritt |
| 2016/0202053 A1 | 7/2016 | Walker et al. |
| 2016/0211045 A1* | 7/2016 | Jeon ............. A61B 6/487 |
| 2016/0213398 A1 | 7/2016 | Liu |
| 2016/0259992 A1 | 9/2016 | Knodt et al. |
| 2016/0278869 A1 | 9/2016 | Grunwald |
| 2016/0296208 A1 | 10/2016 | Sethuraman et al. |
| 2016/0317119 A1* | 11/2016 | Tahmasebi Maraghoosh ............. A61B 8/467 |
| 2016/0374644 A1 | 12/2016 | Mauldin, Jr. et al. |
| 2017/0020561 A1 | 1/2017 | Cox et al. |
| 2017/0079548 A1 | 3/2017 | Silverstein et al. |
| 2017/0143312 A1 | 5/2017 | Hedlund et al. |
| 2017/0164923 A1 | 6/2017 | Matsumoto |
| 2017/0172666 A1 | 6/2017 | Govari et al. |
| 2017/0215842 A1 | 8/2017 | Ryu et al. |
| 2017/0252004 A1 | 9/2017 | Broad et al. |
| 2017/0328751 A1 | 11/2017 | Lemke |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0228465 A1 | 8/2018 | Southard et al. |
| 2018/0235649 A1 | 8/2018 | Elkadi |
| 2018/0235709 A1 | 8/2018 | Donhowe et al. |
| 2018/0289927 A1 | 10/2018 | Messerly |
| 2018/0296185 A1 | 10/2018 | Cox et al. |
| 2018/0310955 A1 | 11/2018 | Lindekugel et al. |
| 2018/0344293 A1 | 12/2018 | Raju et al. |
| 2019/0060001 A1 | 2/2019 | Kohli et al. |

(56) References Cited

U.S. PATENT DOCUMENTS

| | | |
|---|---|---|
| 2019/0060014 A1 | 2/2019 | Hazelton et al. |
| 2019/0125210 A1 | 5/2019 | Govari et al. |
| 2019/0200951 A1 | 7/2019 | Meier |
| 2019/0239848 A1 | 8/2019 | Bedi et al. |
| 2019/0307419 A1 | 10/2019 | Durfee |
| 2019/0307515 A1 | 10/2019 | Naito et al. |
| 2019/0365347 A1 | 12/2019 | Abe |
| 2019/0365348 A1 | 12/2019 | Toume et al. |
| 2020/0069929 A1 | 3/2020 | Mason et al. |
| 2020/0113540 A1 | 4/2020 | Gijsbers et al. |
| 2020/0163654 A1 | 5/2020 | Satir et al. |
| 2020/0200900 A1 | 6/2020 | Asami et al. |
| 2020/0205774 A1* | 7/2020 | Duffy .............. A61B 8/461 |
| 2020/0230391 A1 | 7/2020 | Burkholz et al. |
| 2020/0281563 A1 | 9/2020 | Muller et al. |
| 2020/0359990 A1 | 11/2020 | Poland et al. |
| 2021/0059639 A1 | 3/2021 | Howell |
| 2021/0137492 A1 | 5/2021 | Imai |
| 2021/0161510 A1 | 6/2021 | Sasaki et al. |
| 2021/0186467 A1 | 6/2021 | Urabe et al. |
| 2021/0212668 A1 | 7/2021 | Li et al. |
| 2021/0267570 A1 | 9/2021 | Ulman et al. |
| 2021/0315538 A1 | 10/2021 | Brandl et al. |
| 2022/0039777 A1 | 2/2022 | Durfee |
| 2022/0039829 A1 | 2/2022 | Zijlstra et al. |
| 2022/0071593 A1 | 3/2022 | Tran |
| 2022/0096797 A1 | 3/2022 | Prince |
| 2022/0104791 A1 | 4/2022 | Matsumoto |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0172354 A1 | 6/2022 | Misener et al. |
| 2022/0330922 A1 | 10/2022 | Sowards et al. |
| 2022/0334251 A1 | 10/2022 | Sowards et al. |
| 2023/0107629 A1 | 4/2023 | Sowards et al. |
| 2023/0132148 A1 | 4/2023 | Sowards et al. |
| 2023/0135562 A1 | 5/2023 | Misener et al. |
| 2023/0138970 A1 | 5/2023 | Sowards et al. |
| 2023/0148872 A1 | 5/2023 | Sowards et al. |
| 2023/0201539 A1 | 6/2023 | Howell |
| 2023/0277153 A1 | 9/2023 | Sowards et al. |
| 2023/0277154 A1 | 9/2023 | Sowards et al. |
| 2023/0293143 A1 | 9/2023 | Sowards et al. |
| 2023/0397900 A1 | 12/2023 | Prince |
| 2024/0065673 A1 | 2/2024 | Sowards et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 2823766 A1 | 1/2015 |
| EP | 3181083 A1 | 6/2017 |
| EP | 3870059 | 9/2021 |
| JP | 2000271136 A | 10/2000 |
| JP | 2007222291 A | 9/2007 |
| JP | 2014150928 A | 8/2014 |
| JP | 2018175547 A | 11/2018 |
| KR | 20180070878 A | 6/2018 |
| KR | 102176196 B1 | 11/2020 |
| WO | 2010029521 A2 | 3/2010 |
| WO | 2010076808 A1 | 7/2010 |
| WO | 2013059714 A1 | 4/2013 |
| WO | 2014/115150 A1 | 7/2014 |
| WO | 2015/017270 A1 | 2/2015 |
| WO | 2016081023 A1 | 5/2016 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020067897 A1 | 4/2020 |
| WO | 2020083660 A1 | 4/2020 |
| WO | 2020/186198 A1 | 9/2020 |
| WO | 2021198226 A1 | 10/2021 |
| WO | 2022/072727 A2 | 4/2022 |
| WO | 2022/081904 A1 | 4/2022 |
| WO | 2022/119853 A1 | 6/2022 |
| WO | 2022115479 A1 | 6/2022 |
| WO | 2022119856 A1 | 6/2022 |
| WO | 2022221703 A1 | 10/2022 |
| WO | 2022221714 A1 | 10/2022 |
| WO | 2023059512 A1 | 4/2023 |
| WO | 2023/091424 A1 | 5/2023 |
| WO | 2023076268 A1 | 5/2023 |
| WO | 2023081220 A1 | 5/2023 |
| WO | 2023081223 A1 | 5/2023 |

OTHER PUBLICATIONS

PCT/US2021/045218 filed Aug. 9, 2021 International Search Report and Written Opinion dated Nov. 23, 2021.

PCT/US2021/049123 filed Sep. 3, 2021 International Search Report and Written Opinion dated Feb. 4, 2022.

PCT/US2021/053018 filed Sep. 30, 2021 International Search Report and Written Opinion dated May 3, 2022.

PCT/US2021/060622 filed Nov. 23, 2021 International Search Report and Written Opinion dated Mar. 3, 2022.

PCT/US2021/061267 filed Nov. 30, 2021 International Search Report and Written Opinion dated Mar. 9, 2022.

PCT/US2021/061276 filed Nov. 30, 2021 International Search Report and Written Opinion dated Mar. 9, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 15/951,903, filed Apr. 12, 2018 Board Decision dated Apr. 20, 2022.

U.S. Appl. No. 15/951,903, filed Apr. 12, 2018 Notice of Allowance dated May 2, 2022.

William Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

PCT/US12/61182 International Seach Report and Written Opinion dated Mar. 11, 2013.

PCT/US2021/049294 filed Sep. 7, 2021 International Search Report and Written Opinion dated Dec. 8, 2021.

PCT/US2021/049712 filed Sep. 9, 2021 International Search Report and Written Opinion dated Dec. 14, 2021.

PCT/US2021/052055 filed Sep. 24, 2021 International Search Report and Written Opinion dated Dec. 20, 2021.

U.S. Appl. No. 13/656,563, filed Oct. 19, 2012 Decision on Appeal dated Nov. 1, 2017.

U.S. Appl. No. 13/656,563, filed Oct. 19, 2012 Examiner's Answer dated Nov. 16, 2015.

U.S. Appl. No. 13/656,563, filed Oct. 19, 2012 Final Office Action dated Dec. 5, 2014.

U.S. Appl. No. 13/656,563, filed Oct. 19, 2012 Non-Final Office Action dated Jul. 18, 2014.

U.S. Appl. No. 15/650,474, filed Jul. 14, 2017 Final Office Action dated Jun. 2, 2020.

U.S. Appl. No. 15/650,474, filed Jul. 14, 2017 Non-Final Office Action dated Dec. 16, 2019.

U.S. Appl. No. 15/650,474, filed Jul. 14, 2017 Notice of Allowance dated Dec. 11, 2020.

U.S. Appl. No. 15/650,474, filed Jul. 14, 2017 Notice of Allowance dated Mar. 1, 2021.

U.S. Appl. No. 15/951,903, filed Apr. 12, 2018 Advisory Action dated Dec. 22, 2020.

U.S. Appl. No. 15/951,903, filed Apr. 12, 2018 Examiner's Answer dated Jun. 3, 2021.

(56) References Cited

OTHER PUBLICATIONS

U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2022/025082 filed Apr. 15, 2022 International Search Report and Written Opinion dated Jul. 11, 2022.
PCT/US2022/025097 filed Apr. 15, 2022 International Search Report and Written Opinion dated Jul. 8, 2022.
U.S. Appl. No. 17/020,476, filed Sep. 14, 2020 Final Office Action dated Jun. 9, 2022.
U.S. Appl. No. 17/020,476, filed Sep. 14, 2020 Advisory Action dated Aug. 19, 2022.
U.S. Appl. No. 17/020,476, filed Sep. 14, 2020 Non-Final Office Action dated Sep. 23, 2022.
U.S. Appl. No. 17/471,015, filed Sep. 9, 2021 Non-Final Office Action dated Aug. 16, 2022.
PCT/US2023/014143 filed Feb. 28, 2023 International Search Report and Written Opinion dated Jun. 12, 2023.
PCT/US2023/015266 filed Mar. 15, 2023 International Search Report and Written Opinion dated May 25, 2023.
U.S. Appl. No. 17/684,180, filed Mar. 1, 2022 Non-Final Office Action dated Jul. 28, 2023.
PCT/US2022/048716 filed Nov. 2, 2022 International Search Report and Written Opinion dated Feb. 24, 2023.
PCT/US2022/048722 filed Nov. 2, 2022 International Search Report and Written Opinion dated Feb. 24, 2023.
PCT/US2022/049983 filed Nov. 15, 2022 International Search Report and Written Opinion dated Mar. 29, 2023.
PCT/US2022047727 filed Oct. 25, 2022 International Search Report and Written Opinion dated Jan. 25, 2023.
Saxena Ashish et al Thermographic venous blood flow characterization with external cooling stimulation Infrared Physics and Technology Elsevier Science GB vol. 90 Feb. 9, 2018 Feb. 9, 2018 pp. 8-19 XP085378852.
U.S. Appl. No. 17/020,476, filed Sep. 14, 2020 Final Office Action dated Jan. 5, 2023.
U.S. Appl. No. 17/020,476, filed Sep. 14, 2020 Notice of Allowance dated Apr. 28, 2022.
U.S. Appl. No. 17/468,318, filed Sep. 7, 2021 Non-Final Office Action dated Apr. 12, 2023.
U.S. Appl. No. 17/471,015, filed Sep. 9, 2021 Non-Final Office Action dated Mar. 30, 2023.
U.S. Appl. No. 17/534,099, filed Nov. 23, 2021 Non-Final Office Action dated Mar. 31, 2023.
U.S. Appl. No. 17/684,180, filed Mar. 1, 2022 Restriction Requirement dated May 19, 2023.
EP 20866520.8 filed Apr. 5, 2022 Extended European Search Report dated Aug. 22, 2023.
PCT/US2022/025097 filed Apr. 15, 2021 International Preliminary Report on Patentability dated Oct. 26, 2023.
PCT/US2023/030970 filed Aug. 23, 2023 International Search Report and Written Opinion dated Oct. 30, 2023.
U.S. Appl. No. 17/468,318, filed Sep. 7, 2021 Advisory Action dated Nov. 6, 2023.
U.S. Appl. No. 17/468,318, filed Sep. 7, 2021 Final Office Action dated Sep. 8, 2023.
U.S. Appl. No. 17/471,015, filed Sep. 9, 2021 Final Office Action dated Oct. 12, 2023.
U.S. Appl. No. 17/534,099, filed Nov. 23, 2021 Final Office Action dated Sep. 29, 2023.
U.S. Appl. No. 17/722,151, filed Apr. 15, 2022 Final Office Action dated Nov. 6, 2023.
U.S. Appl. No. 17/722,151, filed Apr. 15, 2022 Non-Final Office Action dated Sep. 7, 2023.
U.S. Appl. No. 17/894,460, filed Aug. 24, 2022 Non-Final Office Action dated Nov. 6, 2023.
U.S. Appl. No. 17/468,318, filed Sep. 7, 2021 Notice of Allowance dated Jan. 18, 2024.
U.S. Appl. No. 17/471,015, filed Sep. 9, 2021 Advisory Action dated Feb. 2, 2024.
U.S. Appl. No. 17/534,099, filed Nov. 23, 2021 Advisory Action dated Dec. 8, 2023.
U.S. Appl. No. 17/538,943, filed Nov. 30, 2021 Non-Final Office Action dated Jan. 30, 2024.
U.S. Appl. No. 17/684,180, filed Mar. 1, 2022 Final Office Action dated Jan. 18, 2024.
U.S. Appl. No. 17/722,111, filed Apr. 15, 2022 Non-Final Office Action dated Dec. 22, 2023.
U.S. Appl. No. 17/722,151, filed Apr. 15, 2022 Advisory Action dated Jan. 2, 2024.
U.S. Appl. No. 17/894,460, filed Aug. 24, 2022 Final Office Action dated Jan. 31, 2024.
M. Ikhsan, K. K. Tan, AS. Putra, C. F. Kong, et al., "Automatic identification of blood vessel cross-section for central venous catheter placement using a cascading classifier," 39th Annual International Conference of the IEEE Engineering in Medicine and Biology Society (EMBC). pp. 1489-1492 (Year: 2017).
U.S. Appl. No. 17/471,015, filed Sep. 9, 2021 Non-Final Office Action dated Mar. 28, 2024.
U.S. Appl. No. 17/534,099, filed Nov. 23, 2021 Non-Final Office Action dated Mar. 14, 2024.
US 17/684, 180 filed Mar. 1, 2022 Advisory Action dated Apr. 4, 2024.
US 17/722, 151 filed Apr. 15, 2022 Non-Final Office Action dated Mar. 25, 2024.
U.S. Appl. No. 17/894,460, filed Aug. 24, 2022 Advisory Action dated Apr. 4, 2024.
U.S. Appl. No. 18/238,281, filed Aug. 25, 2023 Non-Final Office Action dated Mar. 22, 2024.

* cited by examiner

ULTRASOUND PROBE WITH TARGET TRACKING CAPABILITY

PRIORITY

This application claims the benefit of priority to U.S. Provisional Application No. 63/119,829, filed Dec. 1, 2020, which is incorporated by reference in its entirety into this application.

BACKGROUND

There is currently a variety of existing ultrasound systems that include wired or wireless ultrasound probes connected to visual displays. These systems may be used by a clinician to hold and manipulate the ultrasound probe to place a vascular access device (VAD) such as a catheter in a patient. Ultrasound imaging is commonly used for guiding a needle to targets such as veins of the patient. The needle may be monitored in real-time prior and after a percutaneous insertion. This way a clinician may be able to determine the distance and the orientation of the needle to the target vein and ensure accurate insertion with minimal discomfort to the patient. However, inadvertent and unintentional movements of an ultrasound probe during the ultrasound imaging may occur. Such movement may cause the clinician to lose sight of the target vein and the needle. Finding and locating the needle and the target vein to be viewed on a screen of the visual display may be difficult and may waste valuable time. The distance and orientation of the needle right before the percutaneous insertion may be difficult to determine since a needle plane including the needle is perpendicular (or near perpendicular) to an image plane of the ultrasound probe.

It may be easier to monitor the distance and orientation of the needle immediately after the percutaneous insertion when the needle plane is parallel to the image plane. While inadvertently moving or shifting the ultrasound probe, the clinician can lose the vein and/or the needle when adjusting the image plane before and after the percutaneous insertion which can result in a loss of valuable time. The existing ultrasound systems do not provide for convenient needle guidance capability that takes into account the inadvertent movement or shifting the ultrasound probe. Thus, what is needed are a method and system for an ultrasound image target tracking to account for the inadvertent movements or shifting of the ultrasound probe to facilitate efficient needle guidance.

Accordingly, disclosed herein are methods and systems for analyzing ultrasound images to detect targets including anatomic targets and medical devices appearing within an ultrasound imaging area and generating a cropped image to maintain a location of the detected targets in the cropped image in the event of a shift of the ultrasound probe head.

SUMMARY OF THE INVENTION

Briefly summarized, disclosed herein is an ultrasound probe including, in some embodiments, an image target tracking capability. The ultrasound probe system may provide a consistent ultrasound view throughout an ultrasound guided procedure while compensating for inadvertent movements of the ultrasound probe. The exemplary tracking feature advantageously allows for incidental movement of the ultrasound probe during the procedure without drastic movement of the most important imaging data on the screen.

In some embodiments, an ultrasound imaging system is disclosed comprising an ultrasound probe including a transducer array configured to acquire ultrasound images, and a console including a processor and non-transitory computer-readable medium having stored thereon a plurality of logic modules that, when executed by the processor, are configured to perform operations including receiving an ultrasound image, detecting one or more targets within the ultrasound image, and generating a visualization from the ultrasound image to center the one or more detected targets within a displayed portion of the ultrasound image. In some embodiments, generating the visualization includes cropping the ultrasound image to center the one or more detected targets within a displayed portion of the ultrasound image. In some embodiments, generating the visualization includes increasing a magnification of a cropped portion of the ultrasound image to center the one or more detected targets within a displayed portion of the ultrasound image.

In some embodiments, the ultrasound probe is operatively connected to the console via a wired or wireless connection. In some embodiments, the console includes a display, and wherein the plurality of logic modules that, when executed by the processor, are configured to perform further operations including render the visualization of the cropped ultrasound image on a display. In some embodiments, detecting the one or more targets includes distinguishing a component within the ultrasound image according to varying color saturation within the ultrasound image. In specific embodiments, detecting the one or more targets includes identifying each of the one or more targets as a blood vessel, bone, organ or medical device. In other embodiments, identifying each of the one or more targets includes comparing characteristics of each of the one or more targets to thresholds set to define organs, blood vessels, bones or medical devices.

In some embodiments, the characteristics include one or more of a detected pulsatility upon analysis of the ultrasound image and a prior ultrasound image, dimensions of each of the one or more targets or color saturation of each of the one or more targets. In some embodiments, a result of comparing the characteristics to the one or more thresholds is a confidence level for each of the one or more targets indicating a likelihood of an identification of a particular target. In specific embodiments, the plurality of logic modules that, when executed by the processor, are configured to perform further operations including detect that at least a first target of the one or more of the targets is within a threshold distance of an edge of the ultrasound image.

In some embodiments, the plurality of logic modules that, when executed by the processor, are configured to perform further operations including generate an alert indicating to a clinician that the first target is within the threshold of the edge of the ultrasound image. In some embodiments, the alert includes a text notification or an arrow indicating a direction to move the ultrasound probe. In other embodiments, the one or more targets includes a blood vessel and a needle. In yet other embodiments, the one or more targets includes a distal tip of the needle.

In some embodiments, method for obtaining ultrasound images by an ultrasound imaging system is disclosed where the ultrasound imaging system includes an ultrasound probe including a transducer array configured to acquire ultrasound images, and a console including a processor and non-transitory computer-readable medium having stored thereon a plurality of logic modules that, when executed by the processor, are configured to perform operations including receiving an ultrasound image, detecting one or more targets within the ultrasound image, and generating a visualization from the ultrasound image by cropping the ultrasound image around the one or more detected targets. In some embodiments, the method comprises receiving an ultrasound image, detecting one or more targets within the ultrasound image, and generating a visualization from the ultrasound image to center the one or more detected targets within a displayed portion of the ultrasound image. In some embodiments, generating the visualization includes cropping the ultrasound image to center the one or more detected targets within a displayed portion of the ultrasound image. In some embodiments, generating the visualization includes increasing a magnification of a cropped portion of the ultrasound image to center the one or more detected targets within a displayed portion of the ultrasound image.

In some embodiments, the ultrasound probe is operatively connected to the console via a wired or wireless connection. In some embodiments, the console includes a display, and wherein the plurality of logic modules that, when executed by the processor, are configured to perform further operations including render the visualization of the cropped ultrasound image on a display. In some embodiments, detecting the one or more targets includes distinguishing a component within the ultrasound image according to varying color saturation within the ultrasound image. In specific embodiments, detecting the one or more targets includes identifying each of the one or more targets as a blood vessel, bone, organ or medical device. In other embodiments, identifying each of the one or more targets includes comparing characteristics of each of the one or more targets to thresholds set to define organs, blood vessels, bones or medical devices.

In some embodiments, the characteristics include one or more of a detected pulsatility upon analysis of the ultrasound image and a prior ultrasound image, dimensions of each of the one or more targets or color saturation of each of the one or more targets. In some embodiments, a result of comparing the characteristics to the one or more thresholds is a confidence level for each of the one or more targets indicating a likelihood of an identification of a particular target. In specific embodiments, the plurality of logic modules that, when executed by the processor, are configured to perform further operations including detect that at least a first target of the one or more of the targets is within a threshold distance of an edge of the ultrasound image.

In some embodiments, the plurality of logic modules that, when executed by the processor, are configured to perform further operations including generate an alert indicating to a clinician that the first target is within the threshold of the edge of the ultrasound image. In some embodiments, the alert includes a text notification or an arrow indicating a direction to move the ultrasound probe. In other embodiments, the one or more targets includes a blood vessel and a needle. In yet other embodiments, the one or more targets includes a distal tip of the needle.

These and other features of the concepts provided herein will become more apparent to those of skill in the art in view of the accompanying drawings and following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1:
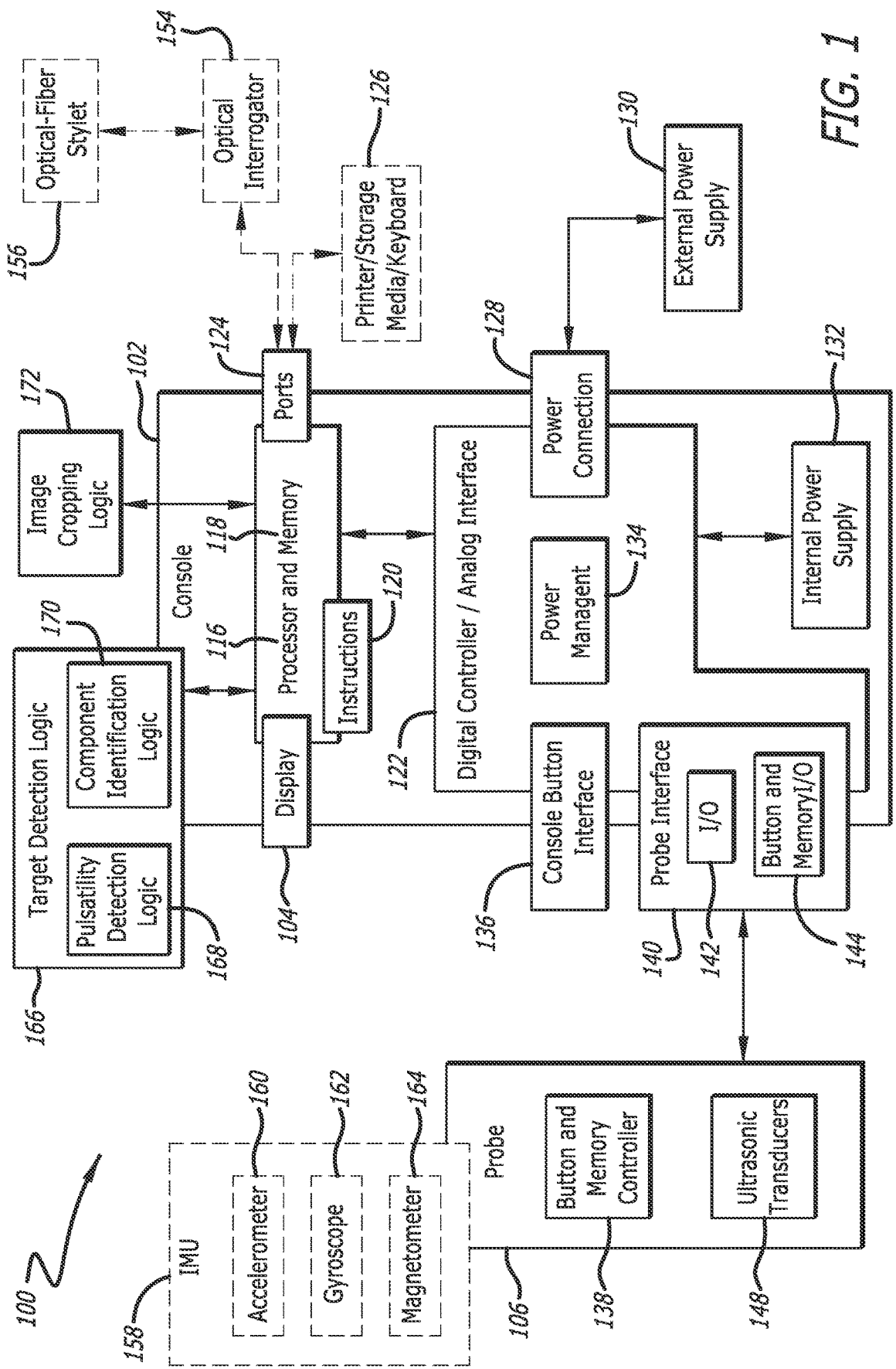
FIG. 1 illustrates a block diagram of the ultrasound imaging system in accordance with some embodiments is shown.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

For clarity, it is to be understood that the word "distal" refers to a direction relatively closer to a patient on which a medical device is to be used as described herein, while the word "proximal" refers to a direction relatively further from the patient. Also, the words "including," "has," and "having," as used herein, including the claims, shall have the same meaning as the word "comprising."

Lastly, in the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

Unless defined otherwise, all technical and scientific terms used herein have the same meaning as commonly understood by those of ordinary skill in the art.

Embodiments disclosed herein are directed to an ultrasound imaging system to be used for ultrasound imaging while placing a needle into a target vein of a patient. The ultrasound imaging system including, in some embodiments, an image target tracking capability is provided. The ultrasound imaging system may provide a consistent ultrasound view throughout an ultrasound guided procedure while compensating for inadvertent movements of an ultrasound probe. The exemplary tracking feature advantageously allows for incidental movement of the ultrasound probe during the procedure without drastic movement of the most important imaging data on the screen. The ultrasound-imaging system, according to the exemplary embodiments, may be primarily used for insertion of an access device such as a needle. The image tracking provides for the precise placement of the needle into a target vein or another anatomic target regardless of the inadvertent movements of the ultrasound probe.

Referring to FIG. 1, a block diagram of the ultrasound imaging system 100 is shown in accordance with some embodiments is shown. The console 102 may house a variety of components of the ultrasound imaging system 100. A processor 116 and memory 118 such as random-access memory (RAM) or non-volatile memory—e.g., electrically erasable programmable read-only memory EEPROM may be included in the console 102 for controlling functions of the ultrasound imaging system 100, as well as for executing various logic operations or algorithms during operation of the ultrasound imaging system 100 in accordance with executable instructions 120 stored in the memory 118 for execution by the processor 116. For example, the console 102 is configured to instantiate by way of the instructions 120 one or more processes for adjusting a distance of activated ultrasonic transducers 148 from a predefined target (e.g., a target vein) or an area, an orientation of the activated ultrasonic transducers 148 to the predefined target or area, or both the distance and the orientation of the activated ultrasonic transducers 148 with respect to the predefined target or area, as well as process electrical signals from the ultrasound probe 106 into ultrasound images. The activated ultrasonic transducers 148 may be adjusted using ultrasound-imaging data, magnetic-field data, fiber-optic shape-sensing data, or a combination thereof received by the console 102. The console 102 may activate certain ultrasonic transducers of a 2-D array of the ultrasonic transducers 148 or moving the already activated transducers in a linear array of the ultrasonic transducers 148.

A digital controller/analog interface 122 may be also included with the console 102 and is in communication with both the processor 116 and other system components to govern interfacing between the ultrasound probe 106 and other system components set forth herein. The ultrasound imaging system 100 further includes ports 124 for connection with additional components such as optional components 126 including a printer, storage media, keyboard, etc. The ports 124 can be implemented as universal serial bus (USB) ports, though other types of ports can be used for this connection or any other connections shown or described herein. A power connection 128 is included with the console 102 to enable operable connection to an external power supply 130. An internal power supply 132 (e.g., a battery) can also be employed either with or exclusive of the external power supply 130. Power management circuitry 134 is included with the digital controller/analog interface 122 of the console 102 to regulate power use and distribution. Optionally, a stand-alone optical interrogator 154 may be communicatively coupled to the console 102 by way of one of the ports 124. Alternatively, the console 102 may include an optical interrogator integrated into the console 502. Such an optical interrogator is configured to emit input optical signals into a companion optical-fiber stylet 156 for shape sensing with the ultrasound imaging system 100. The optical-fiber stylet 156, in turn, may be configured to be inserted into a lumen of a medical device such as the needle and may convey the input optical signals from the optical interrogator 154 to a number of fiber Bragg grating (FBG) sensors along a length of the optical-fiber stylet 156. The optical interrogator 154 may be also configured to receive reflected optical signals conveyed by the optical-fiber stylet 156 reflected from the number of the FBG sensors, the reflected optical signals may be indicative of a shape of the optical-fiber stylet 156.

The optical interrogator 154 may be also configured to convert the reflected optical signals into corresponding electrical signals for processing by the console 102 into distance and orientation information with respect to the target and for dynamically adjusting a distance of the activated ultrasonic transducers 148, an orientation of the activated ultrasonic transducers 148, or both the distance and the orientation of the activated ultrasonic transducers 148 with respect to the target (e.g., a target vein) or the medical device (e.g., a needle) when it is brought into proximity of the target. For example, the distance and orientation of the activated ultrasonic transducers 148 may be adjusted with respect to the vein as the target. An image plane may be established by the activated ultrasonic transducers 148 being disposed at a particular angle to the target vein based on the orientation of the target vein (e.g., perpendicular or parallel among other configurations). In another example, when a medical device such as the needle is brought into proximity of the ultrasound probe 106, an image plane can be established by the activated ultrasonic transducers 148 being perpendicular to a medical-device plane including the needle 204. The distance and orientation information may also be used for displaying an iconographic representation of the medical device on the display.

The display screen 104 may be integrated into (or connected to) the console 102 to provide a GUI and display information for a clinician in a form of ultrasound images of the target acquired by the ultrasound probe 106. In addition, the ultrasound imaging system 100 may enable the distance and orientation of a magnetized medical device such as the needle to be superimposed in real-time atop an ultrasound image of the target, thus enabling a clinician to accurately guide the magnetized medical device to the intended target (e.g., the vein). The display screen 104 can alternatively be separate from the console 102 and communicatively (e.g., wirelessly) coupled thereto. A console button interface 136 may be used to immediately call up a desired mode to the display screen 104 by the clinician for assistance in an ultrasound-based medical procedure. In some embodiments, the display screen 104 may be implemented as an LCD device. The ultrasound probe 106 may optionally include an internal measurement unit (IMU) 158 that may house and accelerometer 160, a gyroscope 162 and a magnetometer 164.

The ultrasound probe 106 may be employed in connection with ultrasound-based visualization of a target such as the vein in preparation for inserting the needle or another medical device into the target. Such visualization gives real-time ultrasound guidance and assists in reducing complications typically associated with such insertion, including inadvertent arterial puncture, hematoma, pneumothorax, etc. The ultrasound probe 106 may be configured to provide to the console 102 electrical signals corresponding to the ultrasound-imaging data, the magnetic-field data, the shape-sensing data, or a combination thereof for the real-time ultrasound needle guidance.

In one embodiment, target detection logic 166 may be executed by the processor 116 to detect vessels and other anatomic targets in the ultrasound images. The target detection logic 166 may include pulsatility detection logic 168 and component identification logic 170. The target detection logic 166 may use pulsatility detection logic 168 and component identification logic 170. The pulsatility detection logic 168 may compare a sequence of images of a vessel to detect pulses indicated by periodic changes in dimensions of the vessel (e.g., expansions in a diameter of the vessel). The target detection logic 106 may also detect bones by identifying tissues with high density based on color saturation in the ultrasound images. The component identification logic 170 may analyze reflection of echoes in each ultrasound image. This can be implemented, for example, using thresholds set to identify organs, blood vessels and bones. The respective logics 166, 168 and 170 may be stored on a non-transitory computer-readable medium of the console 102. An image cropping logic 172 may be executed on the processor 116 to crop images with the detected anatomic target (e.g., a target vein) so the anatomic target is in the center of the cropped image that of a total ultrasound imaging area as will be discussed in more detail herein. Herein, "cropping" may refer to reducing the amount of the ultrasound image that is displayed. Further, cropping may include increasing a magnification of the cropped portion of the ultrasound image. The target detection logic 166 and image cropping logic 172 may collectively be referred to as "console logic" or "logic of the console 102"; however, the term console logic may also include reference to any of the other logic modules illustrated in FIG. 1.

Figure 2A:
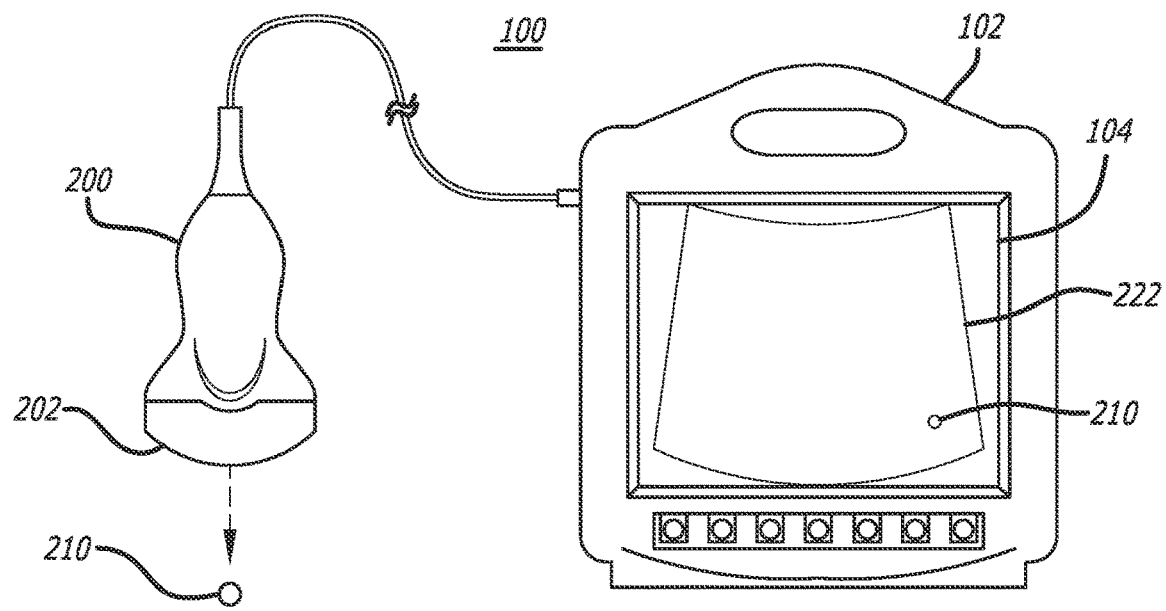
FIG. 2A illustrates a probe connected to a console in accordance with some embodiments.

Referring to FIG. 2A, a probe connected to a console is shown in accordance with some embodiments is shown. In this example, the ultrasound probe 200 is connected to a console 102 over a wired connection. In one embodiment, a wireless connection may be used. The ultrasound probe 200 includes a body that may house a console operatively connected to an ultrasound imaging device 220. The ultrasound probe 200 may be configured to assist a user such as a clinician in insertion of an access device such as a needle into a target vein 210 of a patient. Ultrasonic transducers located in a head 202 of the ultrasound probe are configured to capture 2-D ultrasound images 222 to be displayed on a screen 104 of the console 102. The head 202 may house a linear array of the ultrasonic transducers (not shown) or a 2-D array of the ultrasonic transducers. The ultrasonic transducers may be implemented as piezoelectric transducers or capacitive micro-machined ultrasonic transducers (CMUTs). When the ultrasound probe 200 is configured with the 2-D array of the ultrasonic transducers, a subset of the ultrasonic transducers may be linearly activated as needed for ultrasound imaging based on ultrasound-imaging data being captured.

The transducers may be configured to maintain the target in an image plane or switch to a different image plane (e.g., from a perpendicular plane to a medical-device plane to a plane parallel to the medical-device plane) including the target. If the ultrasound probe 200 is configured with the moveable linear array of the ultrasonic transducers, the ultrasonic transducers may be already activated for ultrasound imaging. For example, a subset of the ultrasonic transducers or all of the available ultrasonic transducers may be moved together on the moveable linear array as needed for ultrasound imaging based on the ultrasound-imaging data to maintain the target in an image plane established by the activated ultrasonic transducers or to switch to a different image plane including the target.

The probe head 202 may be placed against the skin of a patient proximate to a needle-insertion site so the activated ultrasonic transducers in the probe head 202 may generate and emit the generated ultrasound signals into the patient as a sequence of pulses. Then, the transmitters (not shown) may receive reflected ultrasound signals (i.e., reflections of the generated ultrasonic pulses from the patient's body). The reflected ultrasound signals may be converted into corresponding electrical signals for processing into ultrasound images by the console of the probe 200. Thus, a clinician may employ the ultrasound imaging system 100 depicted in FIG. 2A to determine a suitable insertion site and establish vascular access to the target vein 210 with a needle or another medical device.

The ultrasound imaging system 100 depicted in FIG. 2A is capable of target vein 210 visualization in the total available ultrasound image 222 shown on a display 104 of a console 102. In one embodiment, the image data is received from the probe 200 into the console 102 depicted in FIG. 1. The target detection logic 166 may process the image data to render the ultrasound images in the total available ultrasound image 222. As discussed above with reference to FIG. 1, the target detection logic 166 may use pulsatility detection logic 168 and component identification logic 170. The pulsatility detection logic 168 may compare a sequence of images of a vessel to detect pulses indicated by periodic changes in dimensions of the vessel (e.g., expansions in a diameter of the vessel). The component identification logic 170 may also detect bones by identifying tissues with high density based on color saturation in the ultrasound images. The component identification logic 170 may analyze reflection of echoes in each image. This can be implemented using thresholds set to define organs, blood vessels and bones. The respective logics may be stored on a non-transitory computer-readable medium of the console 102. As discussed above, the target detection logic 166 may process the image data including the target vein 210 to render the ultrasound images 222.

The ultrasound imaging system 100 depicted in FIG. 2A may be used for insertion procedure site assessment. Note that while the ultrasound probe assembly depicted in FIG. 2A has a generic shape, the ultrasound probe 200 may be of a different shape as long as the probe captures the insertion site and a target vein 210.

Figure 2B:
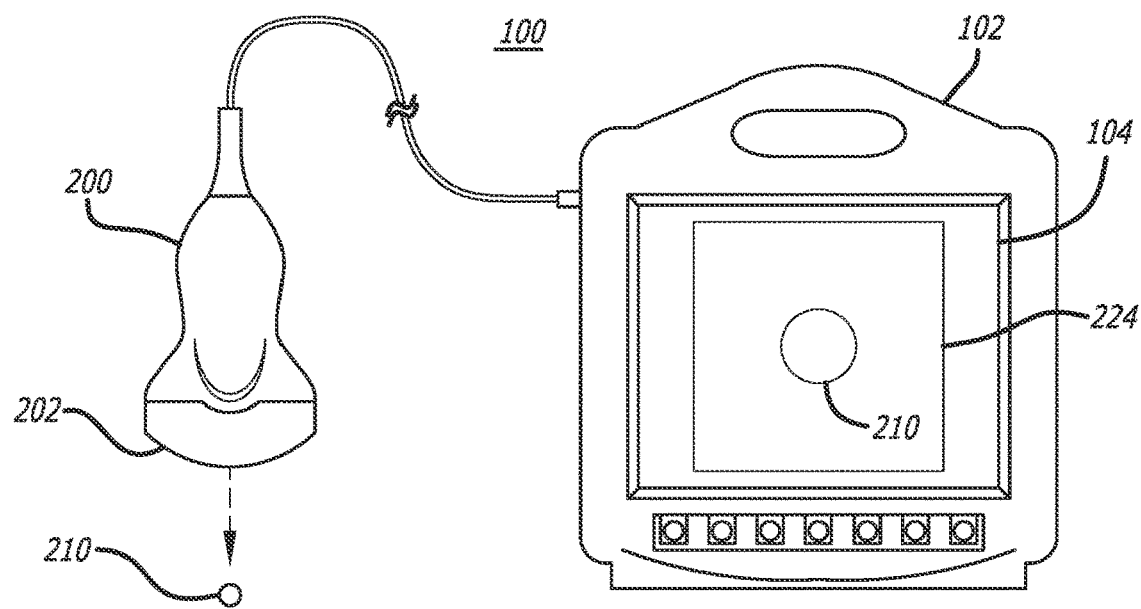
FIG. 2B illustrates a probe connected to a console displaying a target vein in a cropped image in accordance with some embodiments.

Referring to now FIG. 2B, the probe 200 is shown as being connected to the console 102, which is displaying a target vein 210 in a cropped image 224 of a total available ultrasound image. As discussed above with reference to FIG. 2A, the ultrasound probe 200 is connected to the console 102 over a wired connection. In one embodiment, a wireless connection may be used. The ultrasound probe 200 includes a body that may house a console operatively connected to an ultrasound imaging device 220. The ultrasound probe 200 may be configured to assist a user such as a clinician in insertion of an access device such as a needle into a target vein 210 of a patient. The probe head 202 may be placed against the skin of a patient proximate to a needle-insertion site so the activated ultrasonic transducers in the probe head 202 may generate and emit ultrasound signals into the patient as a sequence of pulses. Then, the transmitters (not shown) may receive reflected ultrasound signals (i.e., reflections of the generated ultrasonic pulses from the patient's body). The reflected ultrasound signals may be converted into corresponding electrical signals for processing into ultrasound images by the console of the probe 200. Thus, a clinician may employ the ultrasound imaging system 100 depicted in FIG. 2B to determine a suitable insertion site and establish vascular access to the target vein 210 with a needle or another medical device.

The ultrasound imaging system 100 depicted in FIG. 2B is capable of imaging and detecting a target vein 210 and providing visualizations as a cropped image 320 shown on the display 104 of the console 102. The cropped image 224 is a subset of the total ultrasound image. In one embodiment, the image data is received from the probe 200 by the console 102 as depicted in FIG. 1. The target detection logic 166 running on the console 102 may process the image data to detect an anatomic target (the target vein 210) within the ultrasound images.

The target detection logic 166 may use pulsatility detection logic 168 and component identification logic 170 depicted in FIG. 1. The pulsatility detection logic 168 may compare a sequence of images of a vessel to detect pulses indicated by periodic changes in dimensions of the vessel (e.g., expansions in a diameter of the vessel). The component identification logic 170 may also detect bones by identifying tissues with high density based on color saturation in the ultrasound images. The component identification logic 170 may analyze reflection of echoes in each ultrasound image. This can be implemented using thresholds set to define anatomic targets such as organs, blood vessels, bones, etc. In one embodiment, the image cropping logic 172 depicted in FIG. 1 may crop the ultrasound image capturing the imaging area 300 such that the detected anatomic target (e.g., the target vein 210) is located the center of the cropped image 224. Then, the cropped image 224 includes the vein 210 at its center and is displayed in the display 104 of the console 102. In addition to cropping the ultrasound image capturing the imaging area 300, the cropped image 224 may be magnified to fill, or substantially fill, the display 104. As seen in a comparison of FIGS. 2A-2B, the image of the target vein 210 in FIG. 2B appears larger than the image of the target vein 210 in FIG. 2A, which indicates a magnification has occurred with the cropped image 224.

Figure 3A:
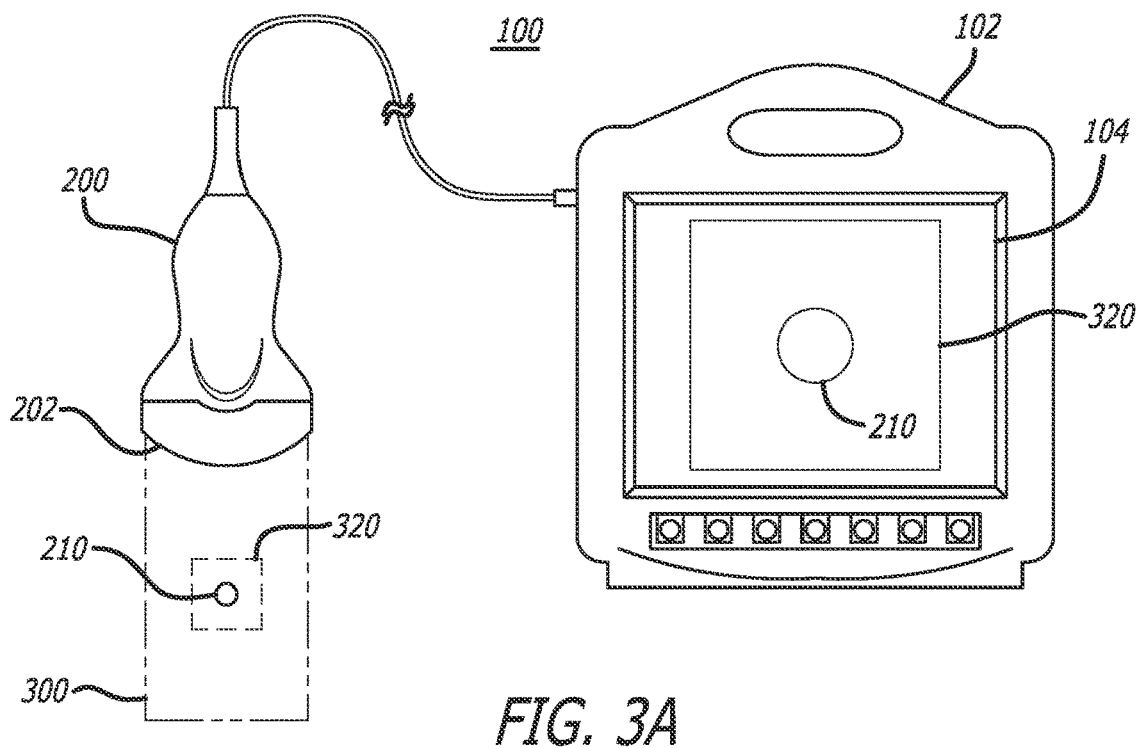
FIG. 3A illustrates a view of visualization of a cropped image of a target vein in a cropped image in accordance with some embodiments.

Referring now to FIG. 3A, a view of a display of a cropped image of a target vein is shown in accordance with some embodiments. As discussed with reference to FIGS. 2A-2B, the ultrasound probe 200 includes a body and a head 202 that houses transducers that may generate and emit the generated ultrasound signals into the patient. The ultrasound imaging system 100 depicted in FIG. 3A is configured to obtain ultrasound images, detect the target vein 210 and render a cropped visualization on a display illustrating of the target vein 210. In this example, the ultrasound probe 200 emits ultrasound pulses causing the ultrasound probe 200 to receive reflected data encompassing an imaging area 300, which includes the target vein 210.

The ultrasound image of the imaging area 300 is provided to the console 102 where the console logic processes the ultrasound image. Specifically, the target detection logic 166 analyzes the ultrasound image to detect the target vein 210. For example, the target detection logic 166 may place a bounding box surrounding the target vein 210 or may detect coordinates of a box around the target vein 210. It should be understood that the term "box" is not limited to a square or rectangle but may refer to any other shape, such as a circle, oval, etc. The image cropping logic 172 then crops the ultrasound image illustrating imaging area 300 around the image of the target vein 210 in such a way that the target vein 210 is located in the center of the cropped image 320. For example, the image cropping logic 172, when executed by the processor 116, may crop the ultrasound image illustrating the imaging area 300 at the bounding box or coordinates determined by the target detection logic 166. Then, the cropped image 320 containing the target vein 210 may be displayed on the screen of the console 102.

Figure 3B:
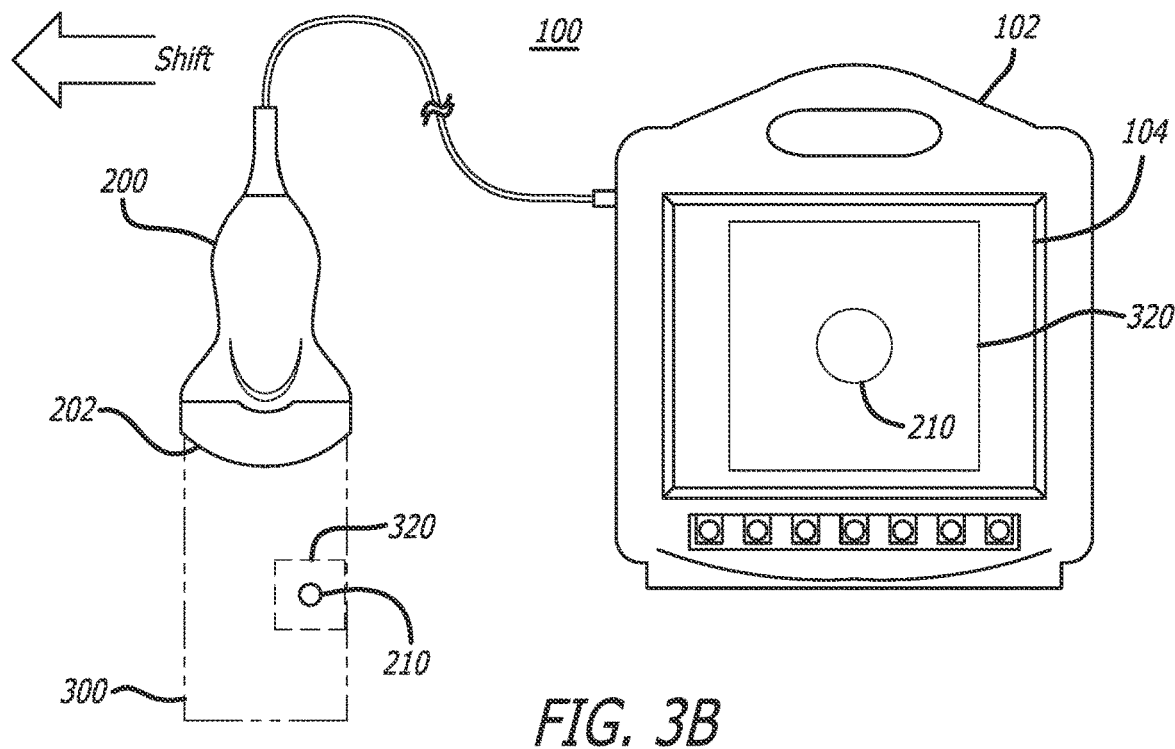
FIG. 3B illustrates a view of visualization of a cropped image of a target vein when the probe shifts in accordance with some embodiments.

Referring to FIG. 3B, a view of visualization of a cropped image of a target vein when the probe shifts is shown in accordance with some embodiments. In this example, the probe 200 inadvertently shifts in a first direction, e.g., to the left. The shift of the probe 200 may produce a corresponding shift of the location of the target vein 210 within the imaging area 300, where the corresponding shift of the target vein 210 may be thought of as being in a second direction opposite the first direction.

However, according to an exemplary embodiment, logic of the ultrasound imaging system 100 is configured to detect the target vein 210 and display an image on the console 102 where the target vein 210 is displayed in the center of the image (i.e., compensating for the shift of the probe 200). Therefore, even as the probe 200 may be inadvertently shifted, the image displayed by the console 102 does maintains the target vein 210 at the center of the displayed image; thus, enabling the clinician to continue focusing on the target vein 210 itself as opposed to focusing on the inadvertent shift of the probe 200.

In other words, the cropped image 320 advantageously does not change in response to the shifting of the probe 200. The ultrasound imaging system 100 may identify and distinguish anatomic targets such as the target vein 210. Then, the ultrasound imaging system 100 may identify the anatomic target and perform image tracking of that target. The console 102 of the ultrasound imaging system 100 may employ console logic (e.g., target detection logic 166 and image cropping logic 172, as referenced above) to receive a sequence of ultrasound images (or a continuous signal) from the probe 200. Further, the console logic may repeatedly detect the target vein 210 within each image and may crop the current image for visualization (e.g., as the cropped image 320). This way, the display of the cropped image 320 of the target vein 210 remains unaffected by the shifting of the probe 200 allowing the clinician to advantageously maintain sight of the visualization of the target vein 210.

Figure 3C:
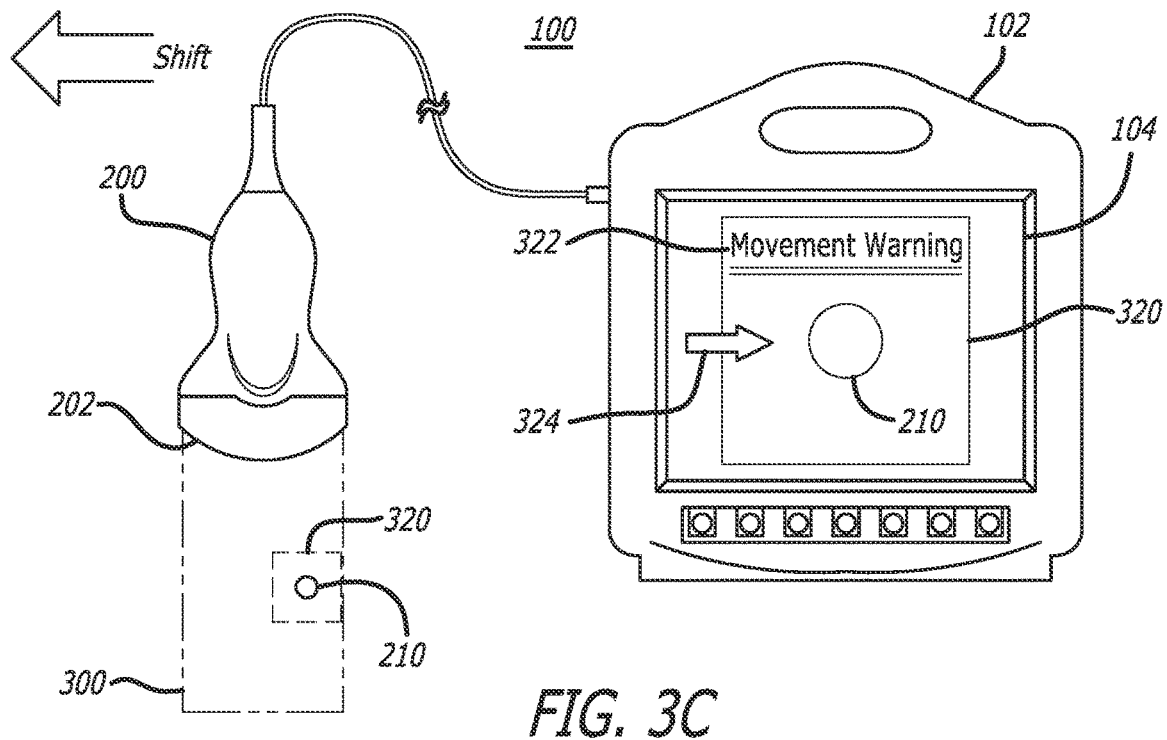
FIG. 3C illustrates a view of visualization of a cropped image of a target vein including a movement warning when the probe shifts in accordance with some embodiments.

Referring now to FIG. 3C, a view of a display of a cropped image of a target vein with a movement warning when the probe shifts is shown in accordance with some embodiments. In one embodiment, the ultrasound imaging system 100 may retain and communicate information on the location of the identified target vein 210. For example, the console logic may determine that a shift of the probe 200 has resulted in the target vein 210 being within a threshold distance from an edge of the imaging area 300 and in response, generate a warning or indication (e.g., such as the warning 322) that is configured to inform the user (e.g., a clinician) that the target vein 210 may soon be out of sight of the probe 200 due to shifts or movement of the probe 200. In some embodiments, the warning or indication may be a visual warning displayed by the console 102 such as the warning 322 as seen in FIG. 3C. The warning 322 may include text, e.g., "Movement warning" and/or an indication of a direction in which to move the probe 200 relative to the target vein 210 (e.g., the arrow 324) in order to more centrally locate the ultrasound imaging area 300 over the target vein 210.

For example, the console logic may detect the target vein 210 in each ultrasound image received from the probe 200. When the ultrasound probe 200 accidentally moves in such a way that the probe head 202 is about to stop capturing the target vein 210, the console logic provides a "movement warning" alert that is displayed on the display 104, e.g., as an overlay on the cropped image 320. The console logic may detect the location of the target vein 210 relative to boundaries of the total ultrasound image area 300. The visual alert may be accompanied by an arrow indicating which way to move the probe to get away from the edge of the screen. This way, the clinician is alerted in time before losing sight of the visualization of the target vein 210. In one embodiment, the "movement warning" alert may be generated by an alert generating logic component of the console logic. In some embodiments, the warning or alert may be an audio alert such as beeping. In some embodiments, the warning or alert may be a vibration of the probe 200, in which case the probe 200 would include a vibration motor that is communicatively coupled to the console logic. In some embodiments, the warning or alert may be any combination of a visual alert, an audio alert and/or a vibration.

Figure 3D:
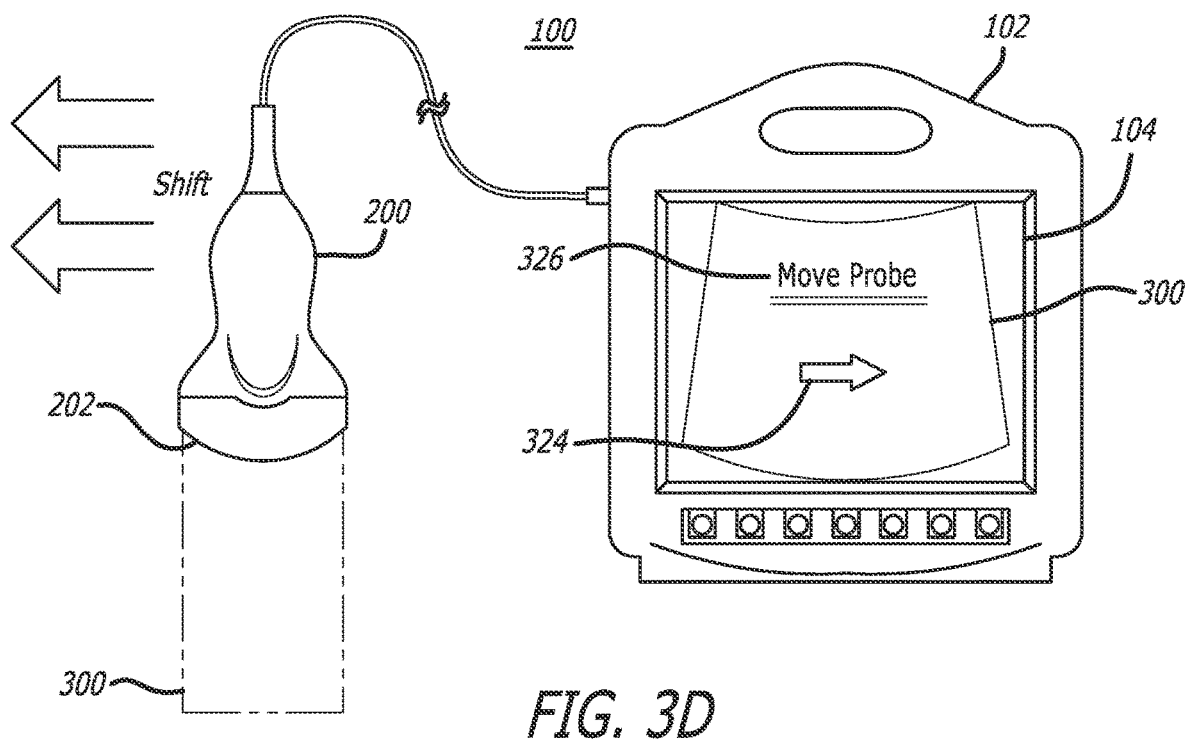
FIG. 3D illustrates a view of a warning message displayed on a console display when the probe shifts and no longer captures the target vein in accordance with some embodiments.

Referring now to FIG. 3D, a view of a warning message displayed on a console display when the probe shifts and no longer captures the target vein is shown in accordance with some embodiments. As discussed above, the ultrasound imaging system 100 may retain and communicate information on the location of the identified target vein 210. For example, the console logic may inform the clinician that the target vein 210 has moved off the screen in a specific direction, e.g., by analyzing an ultrasound image, failing to detect the target vein 210, and generating a visualization to be rendered on the display 104. When the ultrasound probe 200 moves in such a way (shown by double arrows) that it is no longer capturing the target vein 210 (i.e., the target vein is not within the imaging area 300), the console logic can generate an alert configured to be rendered on the display 104 for viewing by the clinician.

In the example depicted in FIG. 3D, console logic may analyze each ultrasound image received from the probe 200 in order to detect the target vein 210. When the ultrasound probe 200 accidentally moves in such a way that the probe head 202 is no longer capturing the target vein 210 (e.g., the target vein 210 is outside of the imaging area 300), the console logic provides a "movement warning" alert that is displayed on the display 104, e.g., as an overlay on the cropped image 320. For instance, the console logic may provide a "Move Probe" message alert 326 that is displayed as an overlay over a rendering of the total imaging area 300. In some embodiments, the console logic may also provide an arrow 324 that indicates the direction in which the probe needs to be moved in order to resume capturing of the target vein 210. This way, the clinician is alerted to move the probe and resume the visualization of the target vein 210.

Figure 4A:
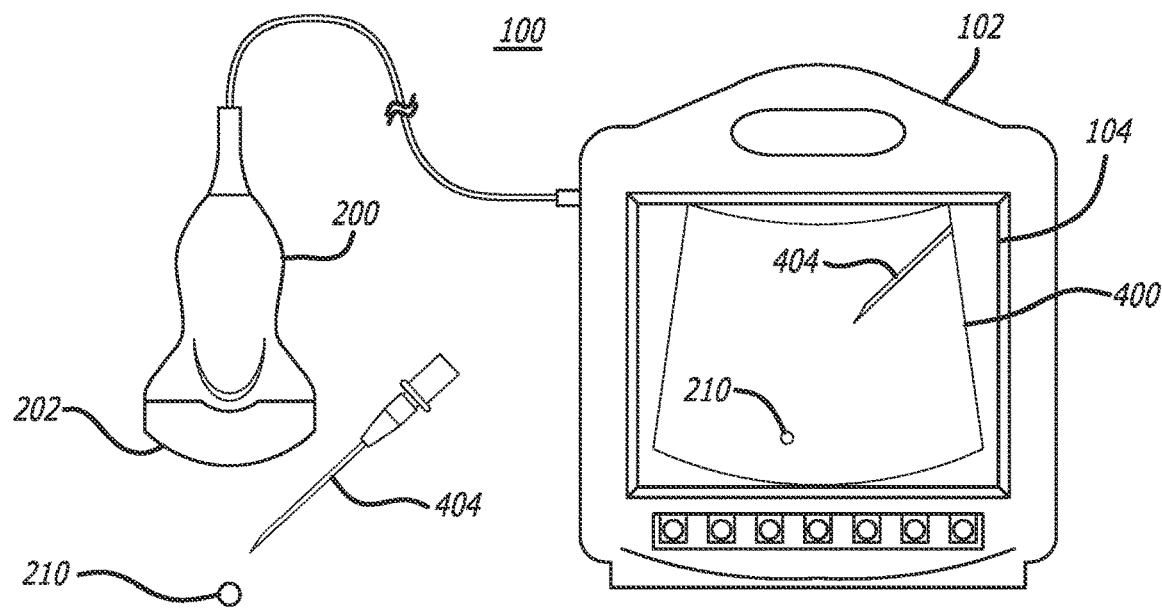
FIG. 4A illustrates a probe connected to a console displaying a target vein and a needle in accordance with some embodiments.

Referring to FIG. 4A, the probe connected to the console of FIG. 2A including imaging of a target vein and a needle is shown in accordance with some embodiments is shown. As noted above, the ultrasound probe 200 may be connected to the console 102 via a wired or wireless connection. As illustrated, the probe head 202 may be placed against the skin of a patient proximate to a needle-insertion site so the activated ultrasonic transducers in the probe head 202 may generate and emit the generated ultrasound signals into the patient as a sequence of pulses. Then, the transmitters (not shown) may receive reflected ultrasound signals (i.e., reflections of the generated ultrasonic pulses from the patient's body). The reflected ultrasound signals may be converted into corresponding electrical signals for processing into ultrasound images by the console of the probe 200. Thus, a clinician may employ the ultrasound imaging system 100 depicted in FIG. 2A to determine a suitable insertion site and establish vascular access to the target vein 210 with a needle or another medical device. Further, the reflected ultrasound signals may include reflections from the needle 404, thus enabling the ultrasound imaging system 100 to display an ultrasound image illustrating the imaging area 400.

Figure 4B:
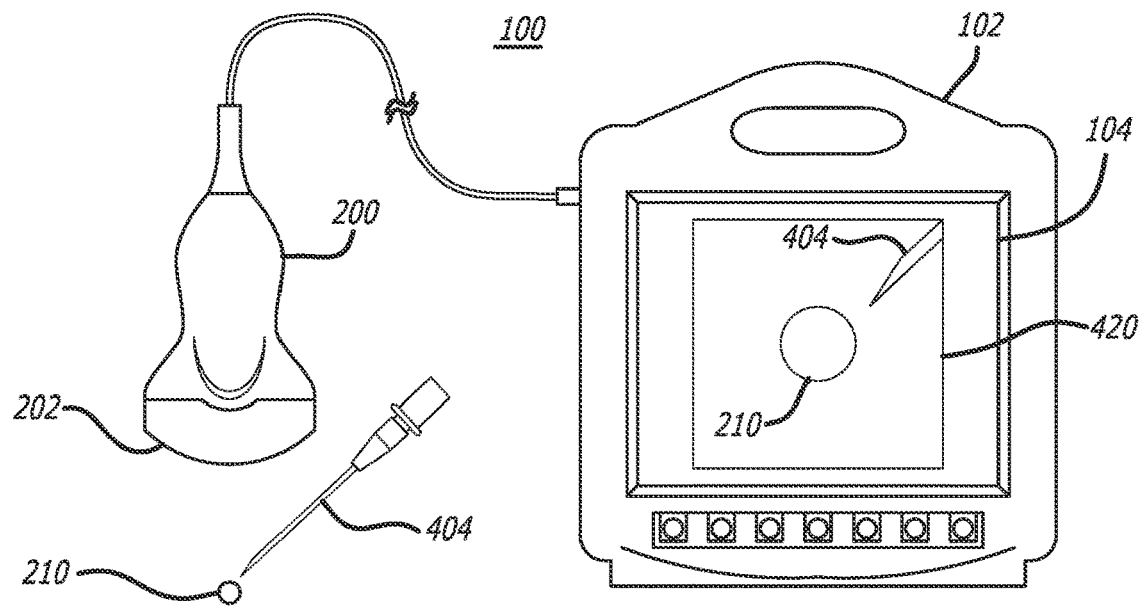
FIG. 4B illustrates a probe connected to a console displaying a target vein and a needle in a cropped image in accordance with some embodiments.

Referring to now FIG. 4B, the probe 200 is shown as being connected to the console 102, which is displaying a target vein 210 and a portion of the needle 404 in a cropped image 420 of a total available ultrasound image. As discussed, the ultrasound imaging system 100 may be configured to obtain an ultrasound image illustrating an ultrasound imaging area 400 and render a cropped image 420 illustrating a portion of the ultrasound imaging area 400 on the display 104 of the console 102. In some such embodiments, target detection logic 166 of the console 102 may process the image data (ultrasound reflection data) to crop the ultrasound images and cause the rendering of the cropped image 420. Specifically, the target detection logic 166 may use pulsatility detection logic 168 and component identification logic 170. The pulsatility detection logic 168 may compare a sequence of images of a vessel to detect pulses indicated by periodic changes in dimensions of the vessel (e.g., expansions in a diameter of the vessel). The component identification logic 170 may also detect bones by identifying tissues with high density based on color saturation in the ultrasound images.

The component identification logic 170 may analyze reflection of echoes in each image. The identification of components may be implemented based on comparing characteristics of detected components (e.g., pulsatility over a plurality of images, dimensions of the detected components, color saturation, etc.) to thresholds set to define organs, blood vessels and bones. Based on the result of comparing the characteristics of detected components to the one or more thresholds, a confidence level (or score) may be determined indicating a likelihood of an identification of a particular component (e.g., a confidence score that a particular detected component is a bone or a blood vessel).

Further and in a similar manner, the target detection logic 166 may also be configured to detect a needle with an ultrasound image. A needle, such as the needle 404, may include specific and known reflection characteristics (e.g., dimensions, color saturation, etc.) such that the component identification logic 170 of the target detection logic 166 may detect and identify a needle in the same manner as discussed with respect to vessel and bone detection. Thus, the ultrasound probe 200 may be configured to assist a user such as a clinician in insertion of an access device, e.g., the needle 404, into a target vein 210 of a patient. The probe head 202 may be placed against the skin of a patient proximate to a needle-insertion site so the activated ultrasonic transducers in the probe head 202 may generate and emit ultrasound signals into the patient as a sequence of pulses. Then, the transmitters (not shown) may receive reflected ultrasound signals (i.e., reflections of the generated ultrasonic pulses from the patient's body). The reflected ultrasound signals may be converted into corresponding electrical signals for processing into ultrasound images by the console of the probe 200. Thus, a clinician may employ the ultrasound imaging system 100 depicted in FIG. 2B to determine a suitable insertion site and establish vascular access to the target vein 210 with a needle or another medical device.

Following detection and identification of components included within the imaging area 400, the ultrasound imaging system 100 may be configured to generate a cropped image, such as the cropped image 420, which includes both the target vein 210 and a portion of the needle 404. In one embodiment, the image cropping logic 172 depicted in FIG. 1 may crop the ultrasound image illustrating the imaging area 400 such that the detected anatomic target (e.g., the target vein 210) is located the center of the cropped image 420. Then, the cropped image 420 includes the vein 210 at its center and is displayed on the display 104 of the console 102. In addition to cropping the ultrasound image 300, the cropped image 420 may be magnified to fill, or substantially fill, the display 104. As seen in a comparison of FIGS. 4A-4B, the image of the target vein 210 in FIG. 4B appears larger than the image of the target vein 210 in FIG. 4A, which indicates a magnification has occurred with the cropped image 420.

In some embodiments, a determination of a boundary at which to crop the ultrasound image illustrating the imaging area 400 includes determination of the positioning of the needle 404 and its distance from the target vein 210. For example, the cropped image 420 may consist of a smaller bounding box surrounding the target vein 210 when the needle 404 is in close proximity to the target vein 210 and consist of a larger bounding box when the needle 404 is further away from the target vein 210. Therefore, in both situations, the cropped image 420 illustrates the target vein 210 and the needle 404. However, in other embodiments, the bounding box upon which the cropped image 420 is created is a predetermined size and cropping would not take into consideration a location of the needle 404. As noted above, it should be understood that the term "box" is not limited to a square or rectangle but may refer to any other shape, such as a circle, oval, etc.

Figure 5A:
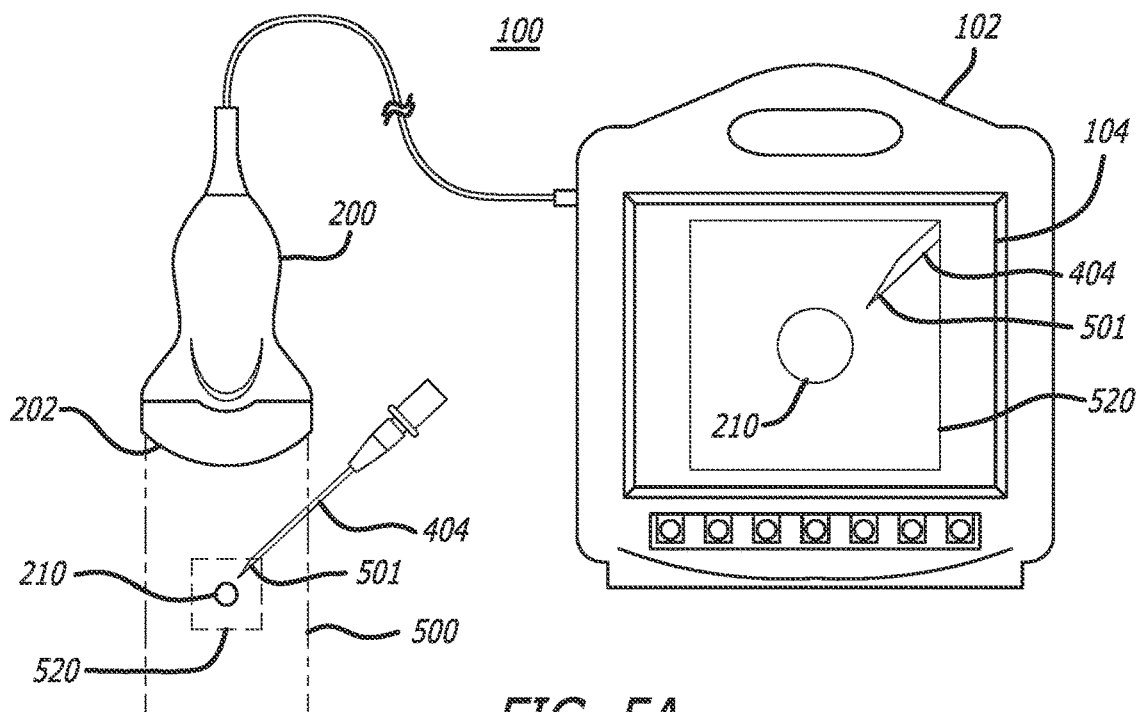
FIG. 5A illustrates a view of visualization of a cropped image of a target vein and tracking of needle projection in accordance with some embodiments.

Referring now to FIG. 5A, a view of a display of a cropped image of a target vein and a portion of a needle is shown in accordance with some embodiments. As discussed with reference to FIGS. 4A-4B, the ultrasound imaging system 100 is configured to obtain ultrasound images, detect the target vein 210 and the needle 404, including the distal tip 501 of the needle 404. Additionally, the ultrasound imaging system 100 may be configured to render a cropped visualization, e.g., the cropped image 520, on a display illustrating of the target vein 210 and the needle 404. In some embodiments, the needle tip tracking can be implemented using the teachings of one or more patents of U.S. Pat. Nos. 5,775,322; 5,879,297; 6,129,668; 6,216,028; and 6,263,230, each of which is incorporated by reference in its entirety into this application.

Figure 5B:
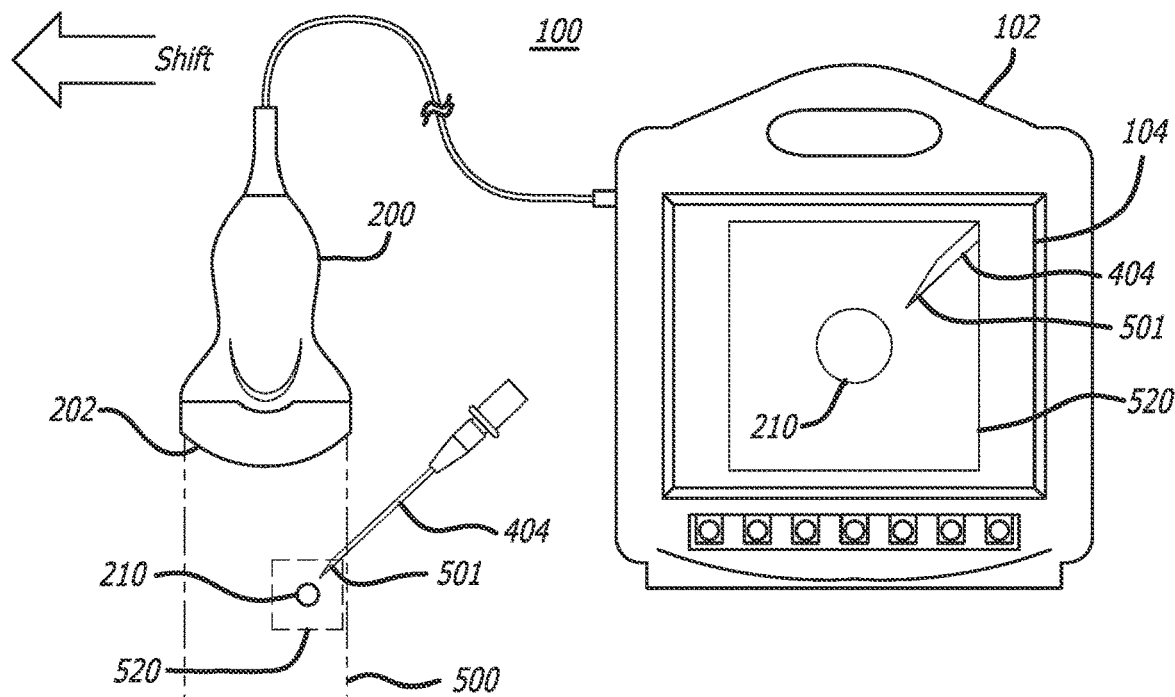
FIG. 5B illustrates a view of visualization of a cropped image of a target vein and tracking of needle projection when the probe shifts in accordance with some embodiments.

Referring to FIG. 5B, a view of visualization of a cropped image of a target vein and a portion of a needle is shown in accordance with some embodiments. In this example, the probe 200 inadvertently shifts in a first direction, e.g., to the left. The shift of the probe 200 may produce a corresponding shift of the location of the target vein 210 within the imaging area 500, where the corresponding shift of the target vein 210 may be thought of as being in a second direction opposite the first direction. However, according to the exemplary embodiment, there is no change occurs in the cropped image 520 of the vein 210 and the distal tip 501 shown to a clinician in the cropped image 520 following the accidental shifting of the probe 200. In other words, the cropped image 520 advantageously does not change in response to the shifting of the probe 200. The ultrasound imaging system 100 may identify and distinguish anatomic targets such as the target vein 210 and the distal tip 501 of the needle 404 in order to perform image tracking of the distal tip 501. The ultrasound imaging system 100 may employ console logic to receive a sequence of ultrasound images (or a continuous signal) from the probe 200. Then, the console logic may repeatedly detect the target vein 210 within each image and may crop the current image for visualization in the cropped image 520. This way the target vein 210 displayed in the cropped image 520 remains unaffected by the shifting of the probe 200. In other words, focus is maintained on the target vein 210 and on the tracking of the needle tip 501. Thus, the clinician advantageously does not lose sight of the visualization of the target vein 210 and tracking of the distal tip 501.

In other words, the cropped image 520 advantageously does not change in response to the shifting of the probe 200. The ultrasound imaging system 100 may identify and distinguish anatomic targets such as the target vein 210. Then, the ultrasound imaging system 100 may identify the anatomic target and perform image tracking of that target. The console 102 of the ultrasound imaging system 100 may employ console logic (e.g., target detection logic 166 and image cropping logic 172, as referenced above) to receive a sequence of ultrasound images (or a continuous signal) from the probe 200. Further, the console logic may repeatedly detect the target vein 210 and the needle 404 within each image and may crop the current image for visualization (e.g., as the cropped image 520). This way, the display of the cropped image 520 of the target vein 210 remains unaffected by the shifting of the probe 200 allowing the clinician to advantageously maintain sight of the visualization of the target vein 210 and the needle 404 as the needle 404 approaches the target vein 210.

Figure 5C:
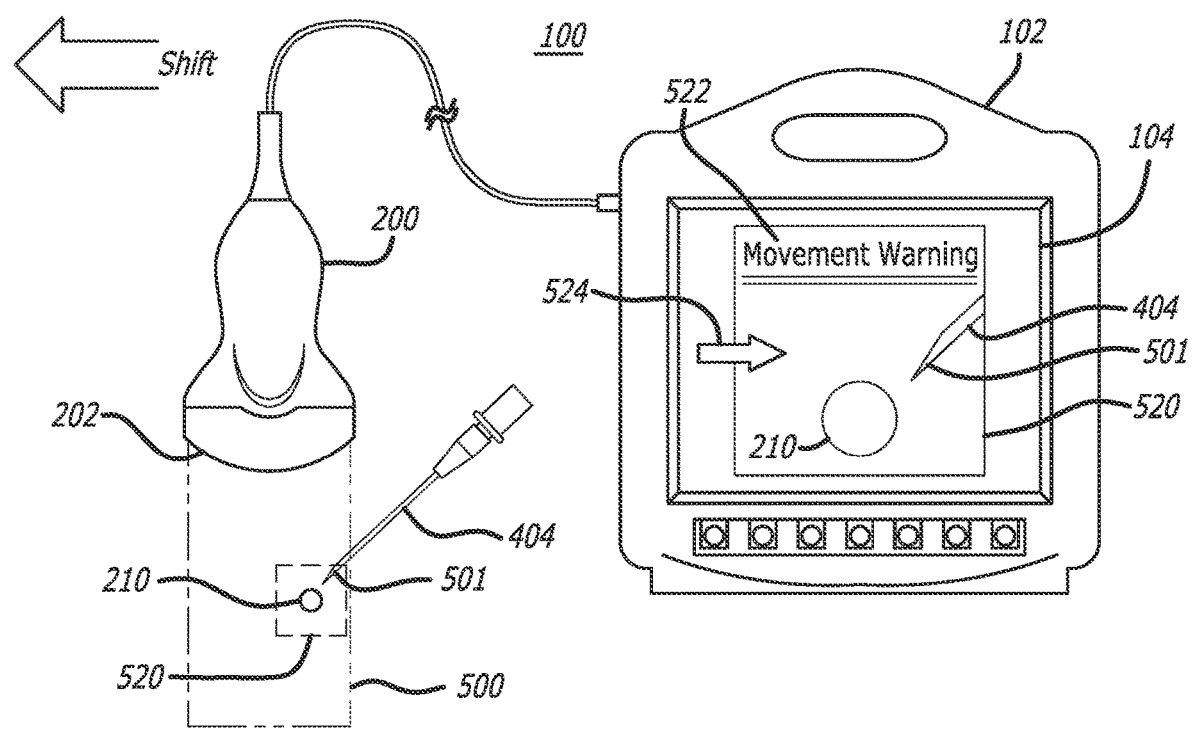
FIG. 5C illustrates a view of visualization of a cropped image of a target vein and tracking of the needle tip projection including a movement warning when the probe shifts is shown in accordance with some embodiments.

Referring now to FIG. 5C, a view of a display of a cropped image of a target vein and a portion of a needle including a movement warning when the probe shifts is shown in accordance with some embodiments. In one embodiment, the ultrasound imaging system 100 may retain and communicate information on the location of the identified target vein 210. For example, the console logic may determine that a shift of the probe 200 has resulted in the target vein 210 and/or a distal tip 501 of the needle 404 being within a threshold distance from an edge of the imaging area 300 and in response, generate a warning or indication (e.g., such as the warning 322) that is configured to inform the user (e.g., a clinician) that the target vein 210 or the distal tip 501 of the needle 404 may soon be out of sight of the probe 200 due to shifts or movement of the probe 200. In some embodiments, the warning or indication may be a visual warning displayed by the console 102 such as the warning 522 as seen in FIG. 5C. The warning 522 may include text, e.g., "Movement warning" and/or an indication of a direction in which to move the probe 200 relative to the target vein 210 (e.g., the arrow 324) in order to more centrally locate the ultrasound imaging area 500 over the target vein 210.

For example, the console logic may detect the target vein 210 and the needle 404, include a distal tip 501 of the needle 404, in each ultrasound image received from the probe 200. When the ultrasound probe 200 accidentally moves in such a way that the probe head 202 is about to stop capturing the target vein 210 or the distal tip 501 of the needle 404, the console logic provides a "movement warning" alert that is displayed on the display 104, e.g., as an overlay on the cropped image 520. The console logic may detect the location of the target vein 210 relative to boundaries of the total ultrasound image area 500. The visual alert may be accompanied by an arrow indicating which way to move the probe to get away from the edge of the screen. This way, the clinician is alerted in time before losing sight of the visualization of the target vein 210 or the distal tip 501 of the needle 404. In one embodiment, the "movement warning" alert may be generated by an alert generating logic component of the console logic. In some embodiments, the warning or alert may be an audio alert such as beeping. In some embodiments, the warning or alert may be a vibration of the probe 200, in which case the probe 200 would include a vibration motor that is communicatively coupled to the console logic. In some embodiments, the warning or alert may be any combination of a visual alert, an audio alert and/or a vibration.

Having a system that not only provides for ultrasound imaging, but ensures that the needle is precisely inserted into a target based on ultrasound image tracking regardless of accidental shifting the ultrasound probe, advantageously reduces a risk of puncturing patient's skin in a wrong place or even in several places.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An ultrasound imaging system comprising:
   an ultrasound probe configured to acquire a series of ultrasound images during a needle insertion procedure; and
   a console communicatively coupled to the ultrasound probe and including a processor and non-transitory computer-readable medium having stored thereon logic that, when executed by the processor, is configured to perform operations including:
      repeatedly receiving ultrasound images comprising the series of ultrasound images acquired by the ultrasound probe during the needle insertion procedure,
      repeatedly detecting a first target blood vessel within the ultrasound images by:
         detecting pulses within the ultrasound images that indicate periodic changes in a dimension of the first target blood vessel,
         detecting that the first target blood vessel of one or more targets detected is within a threshold distance of an edge of a first ultrasound image of the series of ultrasound images, and
         analyzing color saturation within the ultrasound images with respect to one or more thresholds indicative of a blood vessel, and
      generating a visualization from the ultrasound images including (i) determining a bounding box surrounding the first target blood vessel, wherein the first target blood vessel is centered in the bounding box, (ii) cropping the ultrasound images at the bounding box, and (iii) displaying cropped ultrasound images on a display screen during the needle insertion procedure, wherein the display screen is integrated into or connected to the console, and wherein the visualization is repeatedly regenerated during the needle insertion procedure based on repeated receipt of the ultrasound images.

2. The ultrasound imaging system of claim 1, wherein generating the visualization includes increasing a magnification of the cropped ultrasound images to center the one or more targets detected within the cropped ultrasound image.

3. The ultrasound imaging system of claim 1, wherein the ultrasound probe is communicatively connected to the console via a wired or wireless connection.

4. The ultrasound imaging system of claim 1, wherein the console includes the display screen, and wherein the logic that, when executed by the processor, is configured to perform further operations including rendering the visualization of the cropped ultrasound images on the display screen.

5. The ultrasound imaging system of claim 1, wherein detecting the one or more targets includes distinguishing a component within the ultrasound images according to varying color saturation within the ultrasound images.

6. The ultrasound imaging system of claim 1, wherein detecting the one or more targets includes identifying each of the one or more targets as the blood vessel, a bone, an organ or a medical device.

7. The ultrasound imaging system of claim 6, wherein identifying each of the one or more targets includes comparing characteristics of each of the one or more targets to thresholds set to define organs, blood vessels, bones or medical devices.

8. The ultrasound imaging system of claim 7, wherein the characteristics include one or more of a detected pulsatility upon analysis of the first ultrasound image of the series of ultrasound images and a prior ultrasound image of the series of ultrasound images, dimensions of each of the one or more targets or color saturation of each of the one or more targets.

9. The ultrasound imaging system of claim 8, wherein a result of comparing the characteristics to the one or more thresholds is a confidence level for each of the one or more targets indicating a likelihood of an identification of a particular target.

10. The ultrasound imaging system of claim 1, wherein the logic that, when executed by the processor, is configured to perform further operations including: generating an alert indicating to a clinician that the first target blood vessel is within the threshold distance of the edge of the first ultrasound image.

11. The ultrasound imaging system of claim 10, wherein the alert includes a text notification or an arrow indicating a direction to move the ultrasound probe.

12. The ultrasound imaging system of claim 1, wherein the one or more targets includes the blood vessel and a needle.

13. The ultrasound imaging system of claim 12, wherein the one or more targets includes a distal tip of the needle.

14. A method for obtaining ultrasound images by an ultrasound imaging system including an ultrasound probe configured to acquire a series of ultrasound images during a needle insertion procedure, and a console communicatively coupled to the ultrasound probe and including a processor and non-transitory computer-readable medium having stored thereon a logic that, when executed by the processor, is configured to perform operations, the method comprising:
repeatedly receiving ultrasound images comprising the series of ultrasound images acquired by the ultrasound probe during the needle insertion procedure,
repeatedly detecting a first target blood vessel within ultrasound images by:
detecting pulses within the ultrasound images that indicate periodic changes in a dimension of the first target blood vessel,
detecting that the first target blood vessel of one or more targets detected is within a threshold distance of an edge of a first ultrasound image of the series of ultrasound images, and
analyzing color saturation within the ultrasound images with respect to one or more thresholds indicative of a blood vessel, and
generating a visualization from the ultrasound images including (i) determining a bounding box surrounding the first target blood vessel, wherein the first target blood vessel is centered in the bounding box, (ii) cropping the ultrasound images at the bounding box, and (iii) displaying cropped ultrasound images on a display screen during the needle insertion procedure, wherein the display screen is integrated into or connected to the console, and wherein the visualization is repeatedly regenerated during the needle insertion procedure based on repeated receipt of the ultrasound images.

15. The method of claim 14, wherein generating the visualization includes increasing a magnification of the cropped ultrasound images to center the one or more targets detected within the cropped ultrasound images.

16. The method of claim 14, wherein the ultrasound probe is communicatively connected to the console via a wired or wireless connection.

17. The method of claim 14, wherein the console includes the display screen, and wherein the logic that, when executed by the processor, is configured to perform further operations including rendering the visualization of the cropped ultrasound images on the display screen.

18. The method of claim 14, wherein detecting the one or more targets includes distinguishing a component within the ultrasound images according to varying color saturation within the ultrasound images.

19. The method of claim 14, wherein detecting the one or more targets includes identifying each of the one or more targets as the blood vessel, a bone, an organ or a medical device.

20. The method of claim 19, wherein identifying each of the one or more targets includes comparing characteristics of each of the one or more targets to thresholds set to define organs, blood vessels, bones or medical devices.

21. The method of claim 20, wherein the characteristics include one or more of a detected pulsatility upon analysis of the first ultrasound image of the series of ultrasound images and a prior ultrasound image of the series of ultrasound images, dimensions of each of the one or more targets or color saturation of each of the one or more targets.

22. The method of claim 21, wherein a result of comparing the characteristics to the one or more thresholds is a confidence level for each of the one or more targets indicating a likelihood of an identification of a particular target.

23. The method of claim 14, further comprising: generating an alert indicating to a clinician that the first target blood vessel is within the threshold distance of the edge of the first ultrasound image.

24. The method of claim 23, wherein the alert includes a text notification or an arrow indicating a direction to move the ultrasound probe.

25. The method of claim 14, wherein the one or more targets includes the blood vessel and a needle.

26. The method of claim 25, wherein the one or more targets includes a distal tip of the needle.

* * * * *